United States Patent

Schlosser et al.

Patent Number: 5,707,545
Date of Patent: Jan. 13, 1998

[54] CHIRAL OXIRANYLMETHYL ETHERS, AND THEIR USE AS DOPANTS IN LIQUID-CRYSTAL MIXTURES

[75] Inventors: Hubert Schlosser, Glashütten/Taunus; Rainer Wingen, Hattersheim am Main; Anke Kaltbeitzel, Rüsselsheim; Javier Manero, Frankfurt am Main, all of Germany

[73] Assignee: Hoechst Aktiengesellschaft, Frankfurt, Germany

[21] Appl. No.: 256,189

[22] PCT Filed: Aug. 1, 1994

[86] PCT No.: PCT/EP92/02855

§ 371 Date: Jun. 24, 1994

§ 102(e) Date: Jun. 24, 1994

[87] PCT Pub. No.: WO93/13093

PCT Pub. Date: Jul. 8, 1993

[30] Foreign Application Priority Data

Dec. 28, 1991 [DE] Germany .................. 41 43 139.1

[51] Int. Cl.$^6$ .................. C09K 19/34; C09K 19/52; G02F 1/13; C07D 303/08

[52] U.S. Cl. .................. 252/299.61; 252/299.01; 252/299.63; 252/299.64; 252/299.65; 252/299.66; 252/299.67; 428/1; 549/559; 549/560

[58] Field of Search .................. 252/299.61, 299.63, 252/299.01, 299.64, 299.65, 299.66, 299.67; 549/559, 560; 349/182; 428/1

[56] References Cited

U.S. PATENT DOCUMENTS 5,061,814   10/1991   Wand et al. .................. 252/299.01

FOREIGN PATENT DOCUMENTS

| 0 263 437 | 4/1988 | European Pat. Off. . |
| 0 306 919 | 3/1989 | European Pat. Off. . |
| 0 404 981 | 12/1990 | European Pat. Off. . |
| WO 90/11335 | 10/1990 | WIPO . |
| WO 92/11241 | 7/1992 | WIPO . |
| WO 92/12974 | 8/1992 | WIPO . |

*Primary Examiner*—Shean C. Wu
*Attorney, Agent, or Firm*—Curtis, Morris & Safford, P.C.

[57] ABSTRACT

Novel oxiranylmethyl ethers can advantageously be employed in liquid-crystal mixtures since they have high spontaneous-polarization values and features in their molecular structure which make them miscible with other components of liquid-crystal systems.

10 Claims, No Drawings

CHIRAL OXIRANYLMETHYL ETHERS, AND THEIR USE AS DOPANTS IN LIQUID-CRYSTAL MIXTURES

BACKGROUND OF THE INVENTION

1. Field of the Invention

This invention relates to novel chiral oxiranylmethyl ethers and their use as dopants in liquid-crystal mixtures.

2. Description of the Related Art

Particularly in the last decade, liquid crystals have been introduced into various industrial areas in which electro-optical and display-device properties are required (for example in watch, calculator and typewriter displays). These display devices are based on dielectric alignment effects in the nematic, cholesteric and/or smectic phases of the liquid-crystalline compounds, where—caused by the dielectric anisotropy—the molecular long axis of the compounds adopts a preferential alignment in an applied electric field. The usual response times in these display devices are too long for many other potential areas of application of liquid crystals. This disadvantage is particularly noticeable if a large number of pixels must be addressed. Production costs of equipment containing relatively large screen areas, for example of video equipment, are then generally too high.

In addition to nematic and cholesteric liquid crystals, optically active smectic liquid crystal phases have also been increasing in importance over the last few years.

Clark and Lagerwall were able to show that the use of ferroelectric liquid-crystal systems in very thin cells results in electro-optical switching or display elements which have response times faster by a factor of 1000 compared with conventional TN ("twisted nematic") cells (cf., for example, Lagerwall et al., "Ferroelectric Liquid Crystals for Displays", SID Symposium, October Meeting 1985, San Diego, Calif., USA). On the basis of this and other favorable properties, for example the possibility of bistable switching and the virtually viewing angle-independent contrast, FLCs are in principle highly suitable for the abovementioned areas of application, for example via matrix addressing.

For electro-optical or fully optical components, either compounds are required which form tilted or orthogonal smectic phases and are themselves optically active, or ferroelectric smectic phases can be induced by doping compounds which, although forming such smectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S^*_A$ and $S^*_c$ phase can be achieved if the phase sequence of the liquid-crystal mixture is, with decreasing temperature:

isotropic→N*→$S^*_A$→$S^*_c$

The prerequisite is that the pitch of the helix in the N* phase is very large (greater than 10 μm) or even better is fully compensated (see, for example, T. Matsumoto et al., pp. 468–470, Proc. of the 6th Int. Display Research Conf., Japan Display, Sept. 30–Oct. 2, 1986, Tokyo, Japan; M. Murakami et al., ibid. pp. 344–347). This is achieved by adding a further optically active dopant which induces a right-hand helix to the chiral liquid-crystal mixture which has, for example, a left-hand helix in the N* phase, in such amounts that the helix is just compensated.

A further prerequisite for the use of the SSFLCD effect (surface-stabilized ferroelectric liquid-crystal display) of Clark and Lagerwall for uniform planar alignment is that the pitch in the smectic C* phase is significantly greater than the thickness of the display element (Mol. Cryst. Liq. Cryst. 94 (1983), 213–134 and 114 (1984), 151–187). As in the case of the cholesteric pitch, this is achieved by using dopants having the opposite rotation of the helix.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovski in Advances in Liquid Crystal Research and Applications, Oxford/Budapest, 1980, 469 ff.; the PSFLCD effect is described in DE-A 39 20 625 and EP 0 405 346. In contrast to the SSFLCD effect, utilization of these effects requires a liquid-crystalline material having a short $S_c$ pitch.

The optical response time τ [μs] of ferroelectric liquid-crystal systems, which should be as short as possible, depends on the rotational viscosity of the system γ [mPas], the spontaneous polarization $P_s$ [nC/cm$^2$] and the electric field strength E[V/m], in accordance with the equation

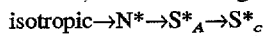

$$\tau \sim \frac{\gamma}{P_s \cdot E}$$

Since the field strength E is determined by the electrode separation in the electro-optical component and by the applied voltage, the ferroelectric display medium must have low viscosity and a high spontaneous polarization to achieve a short response time.

Finally, in addition to thermal, chemical and photochemical stability, a small optical anisotropy Δn, preferably ~0.13, and a low positive or preferably negative dielectric anisotropy Δε are required (see S. T. Lagerwall et al., "Ferroelectric Liquid Crystals for Displays", SID Symposium, Oct. Meeting 1985, San Diego, Calif., USA).

The totality of these requirements can only be achieved by means of mixtures comprising a plurality of components. The base (or matrix) used preferably comprises compounds which if possible themselves already have the desired phase sequence I→N→$S_A$→$S_c$. Further components of the mixture are frequently added in order to reduce the melting point and to broadan the $S_c$ and usually also the N phase, to induce optical activity, for pitch compensation and to match the optical and di-electric anisotropy; however, the rotational viscosity, for example, should if possible not be increased.

Some of these components and also certain mixtures are already known from the prior art. Since, however, the development in particular of ferroelectric liquid-crystal mixtures, can in no way be regarded as complete, the manufacturers of displays are interested in different mixtures, partly also because only the interaction of the liquid-crystalline mixtures with the individual components of the display device or of the cells (for example the alignment layer) allows conclusions to be drawn on the quality of the liquid-crystalline mixtures too.

U.S. Pat. No. 4,705,874 and U.S. Pat. No. 4,638,073 describe liquid-crystalline phenylbenzoates and biphenyls containing chiral oxiranyl-methoxy substituents.

It is furthermore known that chiral oxiranylmethyl ethers of phenyldiazine-2,5-diyls or phenyldiazine-3,6-diyls (EP 0 263 437 and DE 39 09 355) and organosilylalkyl or alkenyl compounds (EP 0 263 437) can be used as dopants in liquid-crystal phases.

OBJECT OF THE INVENTION

The object of the present invention is to indicate compounds which have high inherent or induced polarization values $P_s$ in liquid-crystal phases and have features in their molecular structure which also make them compatible (i.e. miscible) with other components in liquid-crystal systems, since, inter alia, the mesogenic part of the molecules is frequently responsible for good "compatibility" with the other mixture components in liquid-crystal systems; these compounds need not necessarily be liquid-crystalline themselves, in particular need not necessarily have a $S_c$ phase.

SUMMARY OF THE INVENTION

The present invention relates to chiral oxiranylmethyl ethers of the formula (I)

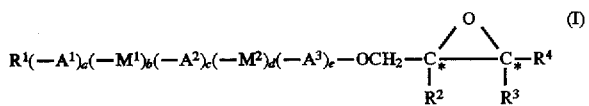

in which the symbols and indices have the following meanings:

* is a center of chirality, $R^1$ is a straight-chain or branched alkyl radical having 1 to 16 carbon atoms (with or without an asymmetric carbon atom), it also being possible for one or more non-adjacent —$CH_2$— groups to be replaced by —O—, —S—, —CO—, —CO—O—, —O—CO—, —CO—S—, —S—CO—, —O—CO—O—, —CH=CH—, —C≡C— or Δ, and/or for one or more H atoms of the alkyl radical to be substituted by F, Cl, Br or CN, or is one of the following chiral groups:

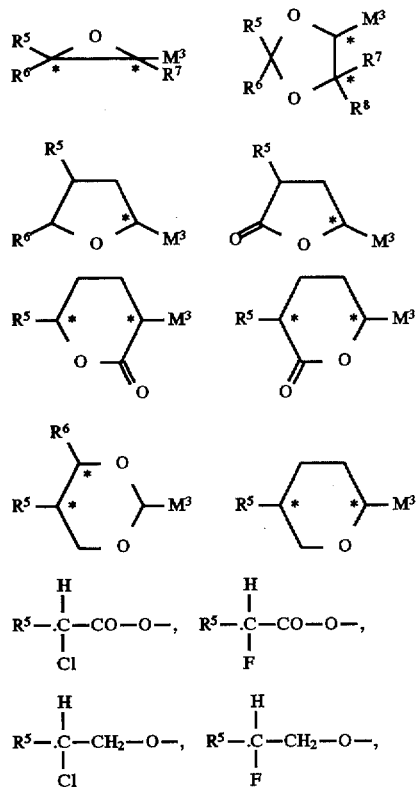

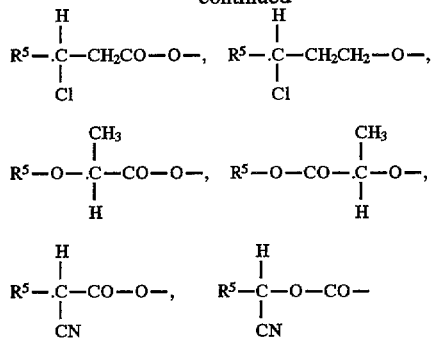

$R^2$, $R^3$, $R^4$, $R^5$, $R^6$, $R^7$ and $R^8$, independently of one another, are H or a straight-chain or branched alkyl radical having 1 to 16 carbon atoms, or $R^5$ and $R^6$ together may alternatively be —$(CH_2)_4$— or —$(CH_2)_5$— if they are bonded as substituents to a dioxolane system;

$A^1$, $A^2$ and $A^3$ are identical or different and are 1,4-phenylene, in which one or two H atoms may be replaced by F, Cl and/or CN, pyrazine-2,5-diyl, pyridazine-3,6-diyl, pyridine-2,5-diyl, pyrimidine-2,5-diyl, trans-1,4-cyclohexylene, in which one or two H atoms may be replaced by CN and/or $CH_3$, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, naphthalene-2,6-diyl, bicyclo-[2.2.2]octane-1,4-diyl or 1,3-dioxaborinane-2,5-diyl;

$M^1$ and $M^2$ are identical or different and are —O—, —S—, —CO—, —CO—O—, —O—CO—, —CO—S—, —S—CO—, —O—CO—O—, —$CH_2$—O—, —O—$CH_2$—, —$CH_2$—$CH_2$—, —CH=CH— or —C≡C—;

$M^3$ is —$CH_2$—O—, —O—$CH_2$—, —CO—O—, —O—CO— or a single bond;

a, b, c, d and e are zero or one, with the proviso that the sum a+c+e is 1,2 or 3;

with the exception of the compounds in which the $(—A^1)_a(—M^1)_b(—A^2)_c(—M^2)_d(—A^3)_e$-group has the following meanings:

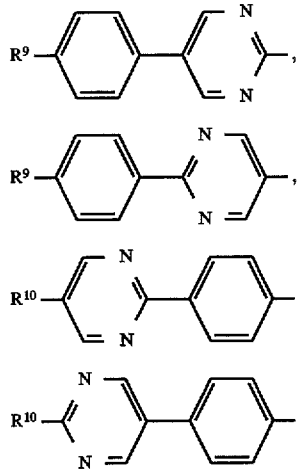

-continued

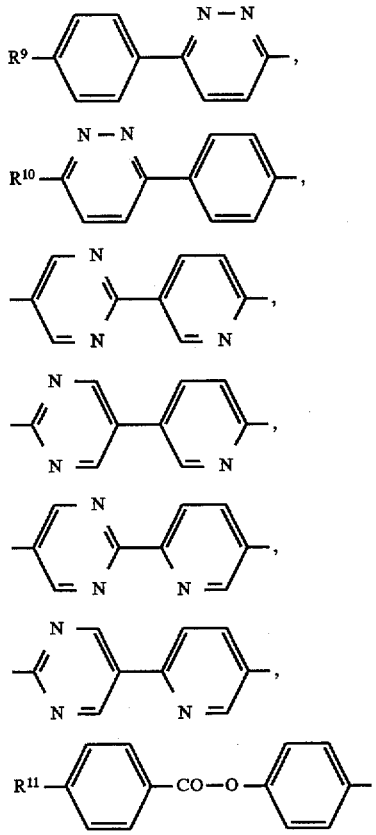

where
R[9] is straight-chain or branched (C$_3$–C$_{12}$)-alkenyl containing a terminal double bond, in which one or two non-adjacent CH$_2$ groups may be replaced by O and/or S atoms, R[10] is as for R[9] or straight-chain or branched alkyl having 1–12 carbon atoms, in which one or two non-adjacent CH$_2$ groups may be replaced by O and/or S, and R[11] is an alkoxy group having 5–12 carbon atoms,

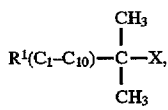

where
X is straight-chain or branched alkylene having 1 to 16 carbon atoms, in which one or two non-adjacent —CH$_2$— groups may also be replaced by —O—, —S—, —O—CO—, —CO—O—, —CO— or —O—CO—O—.

DESCRIPTION OF THE PREFERRED EMBODIMENTS

In the preferred embodiment of the invention, chiral oxiranylmethyl ethers of the formula (I) are employed in which the symbols and indices have the following meanings, with retention of the above-described exceptions:

R[1] is a straight-chain or branched alkyl radical having 1 to 16 carbon atoms (with or without an asymmetric carbon atom), it also being possible for one or more non-adjacent —CH$_2$— groups to be replaced by —O—, —S—, —CO—, —CO—O—, —O—CO—, —O—CO—O—, —CH=CH—, —C≡C— or Δ, or is one of the following chiral groups:

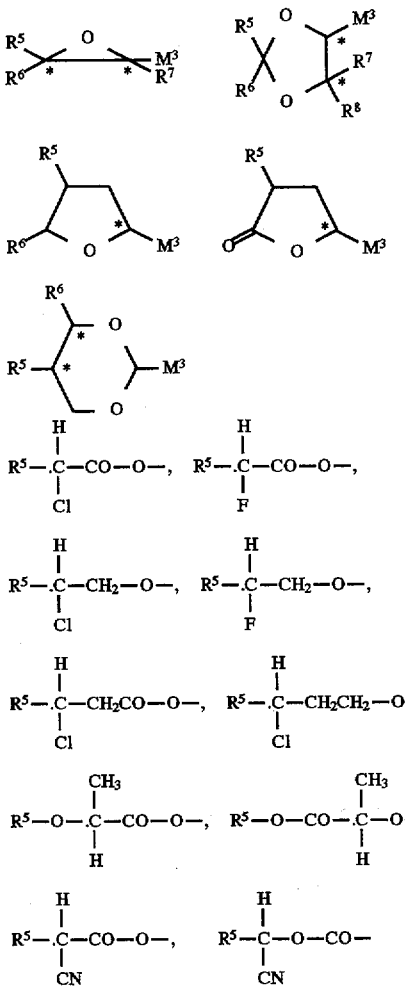

R[2], R[3], R[4], R[5], R[6], R[7] and R[8], independently of one another, are H or a straight-chain or branched alkyl radical having 1 to 16 carbon atoms, where R[5] and R[6] together may alternatively be —(CH$_2$)$_4$— or —(CH$_2$)$_5$— if they are bonded as substituents to a dioxolane system, A[1], A[2] and A[3] are identical or different and are 1,4-phenylene, pyrazine-2,5-diyl, pyridazine-3,6-diyl, pyridine-2,5-diyl, pyrimidine-2,5-diyl, trans-1,4-cyclohexylene, 1,3,4-thiadiazole-2,5-diyl, 1,3-dioxane-2,5-diyl, naphthalene-2,6-diyl or bicyclo[2.2.2]octane-1,4-diyl, M[1] and M[2] are identical or different and are —O—, —CO—, —CO—O—, —O—CO—, —CH$_2$—O—, —O—CH$_2$—, —CH$_2$—CH$_2$—, —CH=CH— or —C≡C—, and M[3] is —CH$_2$—O—, —O—CH$_2$—, —CO—O—, —O—CO— or a single bond.

In a particularly preferred embodiment of the invention, chiral oxiranylmethyl ethers of the formula (I) are employed in which the symbols and indices have the following meanings, with retention of the above-described exceptions:

R[1] is a straight-chain or branched alkyl radical having 1 to 16 carbon atoms (with or without an asymmetric carbon atom), it also being possible for one or two non-adjacent —CH$_2$— groups to be replaced by —O—, —CO—, —CO—O—, —O—CO—, —CH=CH— or Δ, or is one of the following chiral groups:

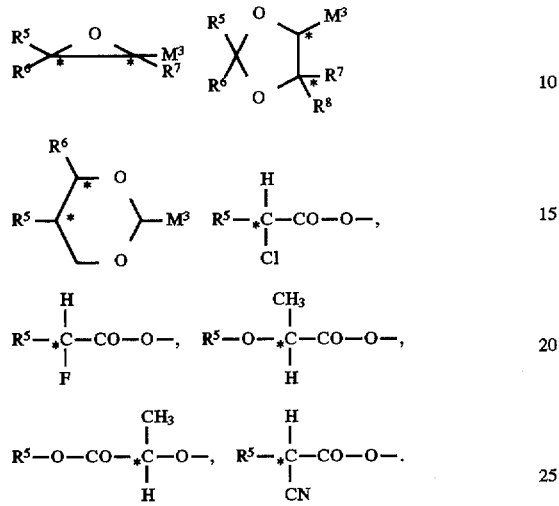

R$^2$, R$^3$, R$^4$, R$^5$, R$^6$, R$^7$ and R$^8$, independently of one another, are H or a straight-chain or branched alkyl radical having 1 to 16 carbon atoms, where R$^5$ and R$^6$ together may alternatively be —(CH$_2$)$_4$— or —(CH$_2$)$_5$— if they are bonded as substituents to a dioxolane system, A$^1$, A$^2$ and A$^3$ are identical or different and are 1,4-phenylene, pyrazine-2,5-diyl, pyridine-2,5-diyl, pyrimidine-2,5-diyl, trans-1,4-cyclohexylene, 1,3,4-thiadiazole-2,5-diyl or naphthalene-2,6-diyl, M$^1$ and M$^2$ are identical or different and are —O—, —CO—O—, —O—CO—, —CH$_2$—O—, —O—CH$_2$—, —CH$_2$—CH$_2$—, —CH=CH— or —C≡C—, and M$^3$ is —CH$_2$—O—, —O—CH$_2$—, —CO—O—, —O—CO— or a single bond.

In an especially preferred embodiment of the invention, chiral oxiranylmethyl ethers of the formula (I) are employed in which, with retention of the above-described exceptions:

R$^1$ is an alkyl radical having 1 to 16 carbon atoms, it being possible for one or two non-adjacent —CH$_2$— groups to be replaced by —O—, Δ or —CH=CH—, or is one of the chiral groups

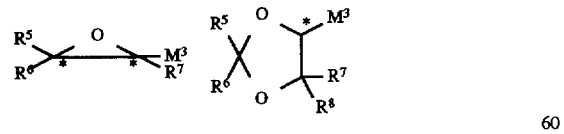

R$^2$, R$^3$, R$^4$, R$^5$ and R$^6$, independently of one another, are H or an alkyl radical having 1 to 16 carbon atoms, M$^3$ is —CH$_2$—O— or —CO—O—, and the (—A$^1$)$_a$(—M$^1$)$_b$(—A$^2$)$_c$(—M$^2$)$_d$(—A$^3$)$_e$— group has the following meanings:

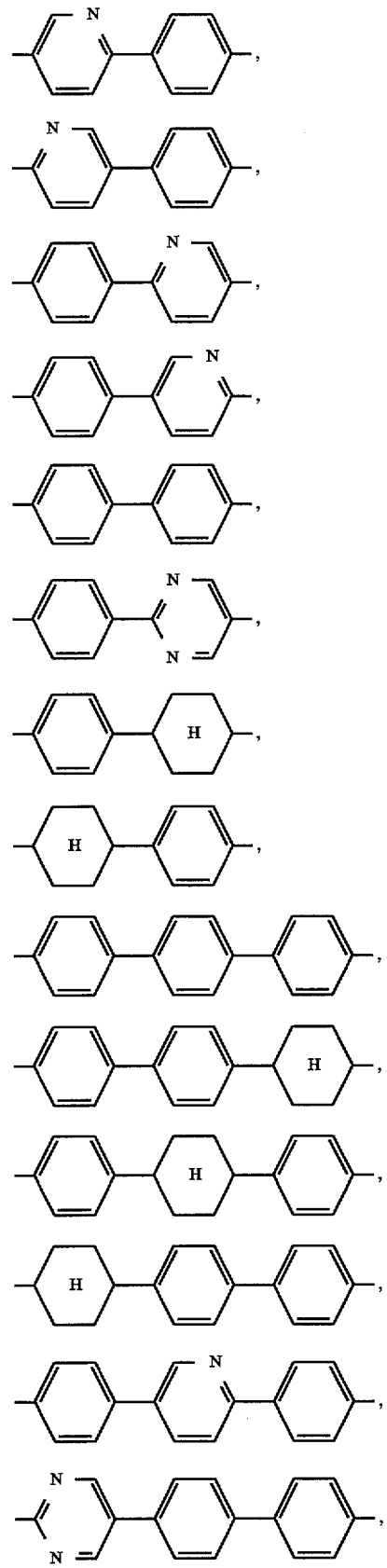

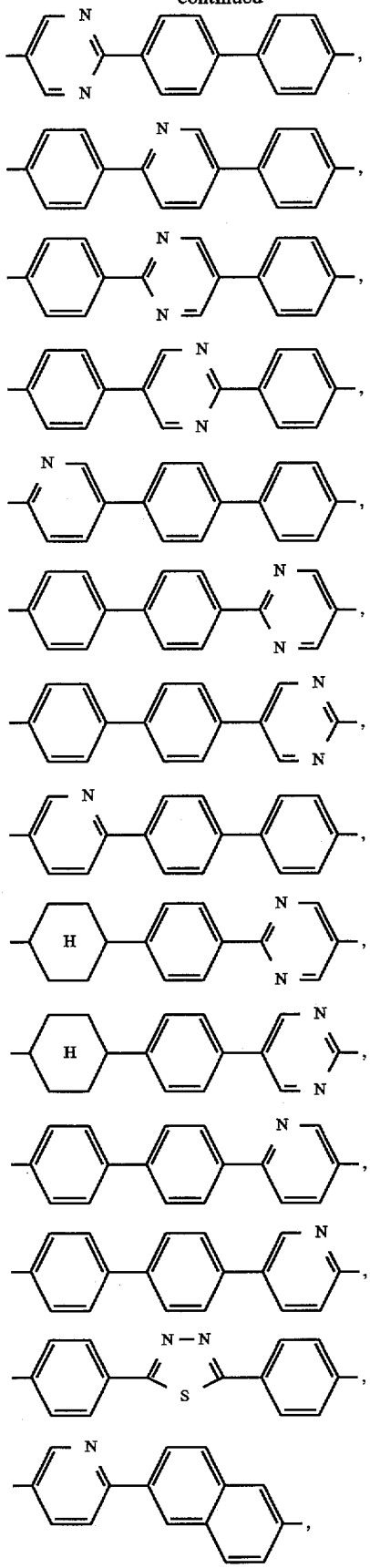
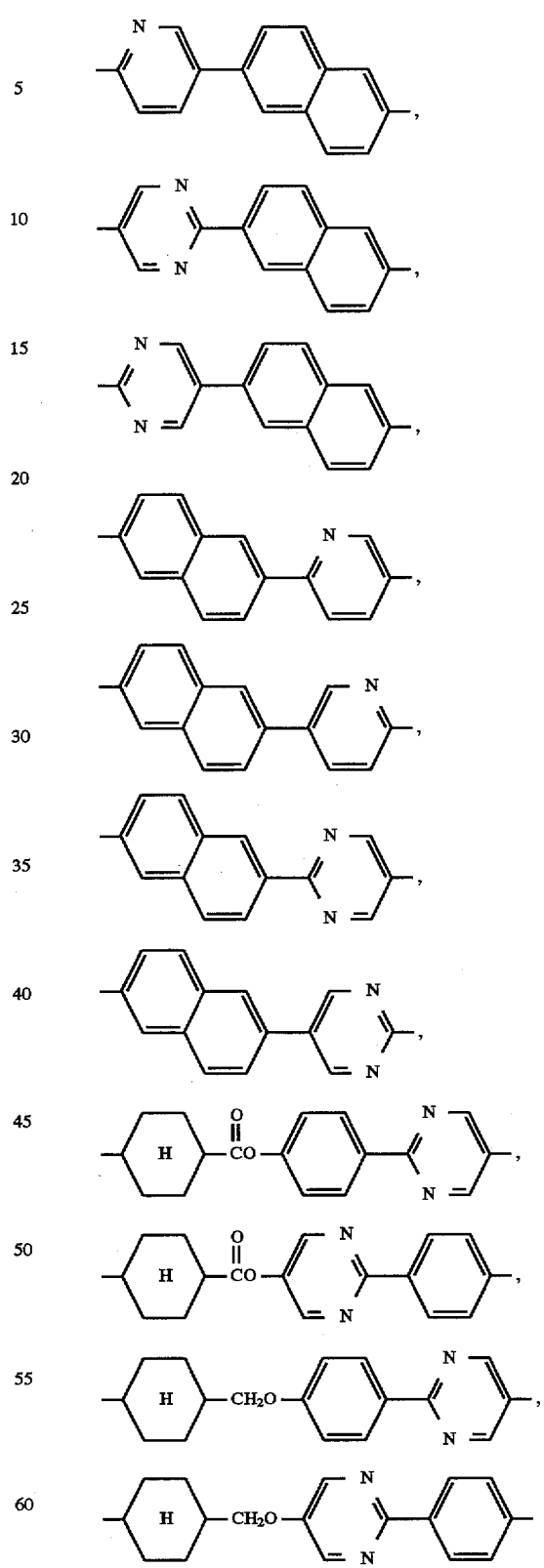
The compounds of the formula (I) can be prepared by reacting the compounds of the formula (IX) with the oxiranes of the formula (X) in which Z is H or a nucleofugic group such as p-toluenesulfonyl, methyl-sulfonyl or trifluoromethylsulfonyl.

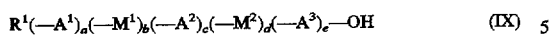     (IX)

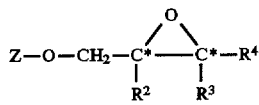     (X)

These reactions can be carried out by methods known per se from the literature (see, for example, Houben-Weyl, Methoden der Organischen Chemie, Georg Thieme Verlag, Stuttgart; O. Mitsunobu, "The Use of Diethyl Azodicarboxylate and Triphenylphosphine in the Synthesis and Transformation of Natural Products", Synthesis 1981, pp. 1–28).

The compounds (IX) and (X) are known from the literature. Thus, for example, the oxiranes (X) where Z is H can be prepared from the corresponding allyl alcohols by enantioselective epoxidation (see, for example, Pfeuniger, "Asymmetric Epoxidation of Allylic Alcohols: The Sharpless Epoxidation", Synthesis 1986, pp. 89–116). They are then employed as such or converted into the corresponding compounds (X) where Z is $H_3CC_6H_4SO_2$ by standard methods, for example by reaction with p-toluenesulfonyl chloride. An analogous situation applies to the other nucleofugic groups mentioned.

Said oxiranylmethyl ethers are suitable as components of liquid-crystal mixtures. The LC mixtures can contain from 0.01 to 60% by weight, preferably from 0.1 to 20% by weight, particularly preferably from 0.1 to 5% by weight, of the compounds according to the invention. The other constituents are preferably selected from known compounds having nematic, cholesteric and/or smectic phases; these include, for example, Schiff bases, biphenyls, terphenyls, phenylcyclohexanes, cyclohexylbiphenyls, N-, S- or O-containing heterocyclic compounds, for example pyrimidines, cinnamic esters, cholesterol esters or various bridged, polycyclic esters of p-alkylbenzoic acids with terminal polar groups. In general, the commercially available liquid-crystal mixtures are, even before addition of the optically active compound(s), mixtures of various components, of which at least one is mesogenic, i.e. as the compound, in derivatized form or in a mixture with other components exhibits a liquid-crystal phase which gives rise to expectations of at least one enantiotropic (clearing point>melting point) or monotropic (clearing point<melting point) mesophase formation.

The compounds according to the invention are particularly suitable as dopants for tilted smectic liquid-crystal phases, since they convert these into ferroelectric liquid-crystal phases.

Liquid-crystal mixtures containing the compounds according to the invention can be employed, for example, in electro-optical or fully optical components, for example as display devices, for image processing, information processing, data storage or generally in the area of nonlinear optics.

In addition, the elements contain the following components:

two electrodes, two outer plates and at least one alignment layer. The structure of FLC displays is described in general terms in EP-B 0 032 362.

The invention is described in greater detail by the examples below:

For the ferroelectric liquid-crystal mixtures, the values for spontaneous polarization $P_s[nC/cm^2]$, the electrical response time $\tau$ [µs] and the helical twisting power in the nematic phase were determined, the first two measurements being carried out at a temperature of 20° C.

The $P_s$ values were measured by the method of H. Diamant et al. (Rev. Sci. Instr., 28, 30, 1957), using measurement cells having an electrode separation of 10 µm without an alignment layer.

In order to measure the electrical response time, a rectangular voltage of ±100 volts was applied to the measurement cell described above, and the polarization reversal current was measured. The electrical response time $\tau$ is defined as the time delay between reversal of the voltage And the maximum polarization current.

The helical twisting power (HTP) in the nematic phase was determined by the Grandjean-Cano method using a wedge cell (F. Grandjean, CR Acad. Sci. (Paris) 172, 71 (1921), R. Cano, Bull. Soc. Franc. Mineral. Crystallogr. XC 333 (1967)).

The phase-transition temperatures were determined with the aid of a polarizing microscope from the changes in structure on heating. By contrast, the melting point was determined using a DSC instrument. The phase-transition temperatures given between the phases
nematic (N or N*)
smectic C ($S_c$ or $S_c$ *)
smectic A ($S_A$)
crystalline (X)
are in °C., and the values are between the phase designations in the phase sequence.

EXAMPLE 1

[(2S,3S)-3-Butyloxiran-2-yl]methyl 4-(5-(4-hexylphenyl)-pyrimidin-2-yl)phenyl ether 0.67 g (3.84 mmol) of diethyl azodicarboxylate are added dropwise at 0° C. to 0.01 g (3.84 mmol) of triphenylphosphine in 50 ml of THF, and the mixture is stirred at 0° C. for 0.5 hour. 1.28 g (3.84 mmol) of 5-(4-hexylphenyl)-2-(4-hydroxyphenyl)pyrimidine and 0.50 g (3.84 mmol) of (2S, 3S)-3-butyloxiran-2-ylmethanol are subsequently added, and the mixture is stirred at room temperature for 17 hours. After evaporation of the reaction mixture, the product is purified by chromatography (silica gel, dichloromethane-:ethyl acetate=9:1) and by recrystallization from acetonitrile.

1.17 g of [(2S,3S)-3-butyloxiran-2-yl]methyl 4-(5-(4-hexylphenyl) pyrimidin-2-yl)phenyl ether having $[\alpha]_D^{20}$ (c=2.37 in $CH_2Cl_2$)=−17.00° are obtained.

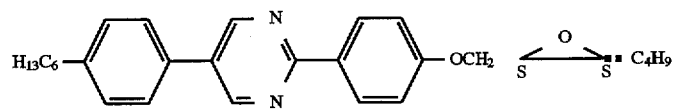

The compound has the following phase sequence:

X 126 $S_c$ * 158–164 $S_A$ 198 I

EXAMPLE 2

[(2S,3S)-3-Butyloxiran-2-yl]methyl 4-(4-(5-octylpyrimidin-2-yl)phenyl)phenyl ether 0.76 g (2.91 mmol) of triphenylphosphine, 0.51 g (2.91 mmol) of diethyl azodicarboxylate, 0.70 g (1.94 mmol) of 2-(4'-hydroxy-4-biphenyl)-5-octylpyrimidine and 0.38 g (2.91 mmol) of (2S,3S)-3-butyloxiran-2-ylmethanol are reacted analogously to Example 1 to give 0.65 g of [(2S,3S)-3-buCyloxiran-2-yl]methyl 4-(4-(5-octylpyrimidin-2-yl)phenyl)phenyl ether having $[\alpha]_D^{20}$ (c=2.68 in $CH_2Cl_2$)= −15.86°.

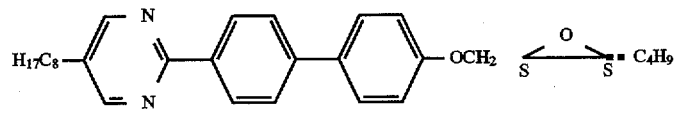

The compound has the following phase sequence:
X 117 (132) $S_2$ 142 $S_c$ * 169 N 184 I

EXAMPLE 3

[(2S,3S)-3-Butyloxiran-2-yl]methyl 4-{5-(2S,3S)-3-butyloxiran-2-ylmethoxypyrimidin-2-yl}phenyl ether

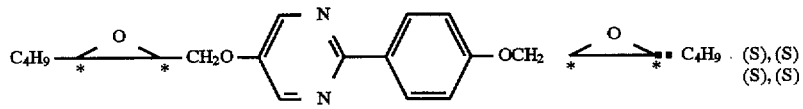

is obtained analogously to Example 1 by reacting [(2S,3S)-3-butyl-2-yl]methyl 4-(5-hydroxypyrimidin-2-yl)phenyl ether—obtained analogously to Example 1 from 5-benzyloxy-2-(4-hydroxyphenyl)pyrimidine and (2S,3S)-3-butyloxiran-2-ylmethanol with subsequent removal of the benzyl group by hydrogenolysis—with (2S,3S)-3-butyloxiran-2-ylmethanol.

The compound has the following phase sequence:
X 89 $S_c$ * 112.5 I

EXAMPLE 4

[(2S,3S)-3-Propyloxiran-2-yl]methyl 2-(4-hexyloxyphenyl)-pyrimidin-5-yl ether

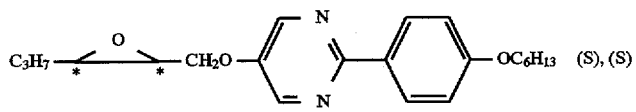

is obtained analogously to Example 1 from 2-(4-hexyloxyphenyl)-5-hydroxypyrimidine and (2S,3S)-3-propyloxiran-2-ylmethanol.

The compound has the following phase sequence:
X 92 $S_c$ * 98 $S_A$ 107 N* 109 I

EXAMPLE 5

[(2S,3S)-3-Butyloxiran-2-yl]methyl 2-(6-octyloxynaphthalen-2-yl)pyrimidin-5-yl ether

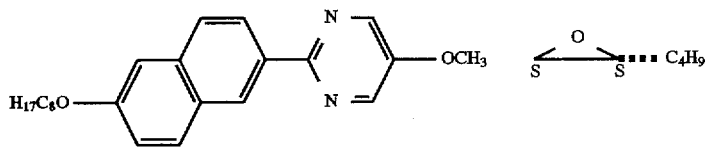

The synthesis is carried out analogously to Example 1 from 5-hydroxy-2-(6-octyloxynaphthalen-2-yl)pyrimidine and (2S,3S)-3-butyloxiran-2-ylmethanol.
The compound has the phase sequence:

X 85 (55) $S_c$ ∗ 128.4 $S_A$ 130.6 N* 141 I $[\alpha]_D^{20}$=−15.67°

EXAMPLE 6

[(2S,3R)-3-Propyloxiran-2-yl]methyl 2-(4-(trans-4-pentyl-cyclohexyl)phenol)pyrimidin-5-yl ether

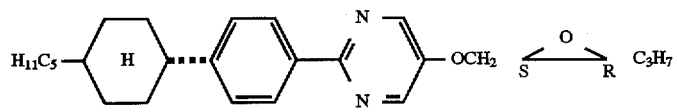

The synthesis is carried out analogously to Example 1 from 5-hydroxy-2-[4-(trans-4-pentylcyclohexyl)phenyl]-pyrimidine and (2S,3R)-3-proploxiran-2-ylmethanol.
The compound has the phase sequence:

X 67 (70) N* 112 I $[\alpha]_D^{20}$=−4.01°

EXAMPLE 7

[(2S,3S)-3-Butyloxiran-2-yl]methyl 2-(4-(trans-4-octylcyclohexyl)phenyl)pyrimidin-5-yl ether

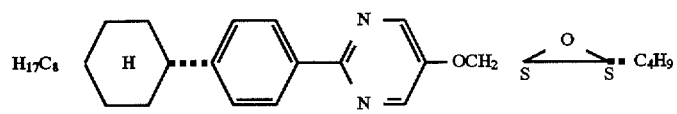

The synthesis is carried out analogously to Example 1 from 5-hydroxy-2-[4-(trans-4-octylcyclohexyl)phenyl]-pyrimidine and (2S,3S)-3-butyloxiran-2-ylmethanol.
The compound has the phase sequence:

X 92 (62) $S_1$ 84 (79) $S_2$ 111 $S_A$ 156 N* 173 I $[\alpha]_D^{20}$=−16.65°

EXAMPLE 8

[(2S,3S)-3-Butyloxiran-2-yl]methyl 4'-(trans-4-propylcyclohexyl)biphenyl-4-yl ether

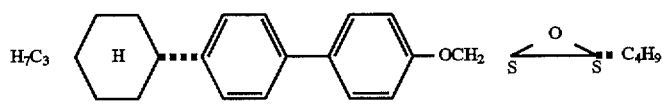

The synthesis is carried out analogously to Example 1 from 4-hydroxy-4'-(trans-4-propylcyclohexyl)biphenyl and (2S,3S)-3-butyloxiran-2-ylmethanol.
The compound has the phase sequence:
X 120 S₁ 82 S₂ 178 S_A 190 N* 197 I [α]_D²⁰=−15.35°

EXAMPLE 9

[(2S,3S)-3-Butyloxiran-2-yl]methyl 2-(4-(trans-4-pentylcyclohexyl)phenyl)pyrimidin-5-yl ether

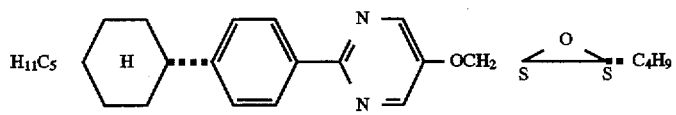

The synthesis is carried out analogously to Example 1 from 5-hydroxy-2-[4-(trans-4-pentylcyclohexyl)phenyl]-pyrimidine and (2S,3S)-3-butyloxiran-2-ylmethanol.
The compound has the phase sequence:
X 107 S_c * 123 N* 186 I [α]_D²⁰=−16.86°

EXAMPLE 10

[(2S,3S)-3-Butyloxiran-2-yl]methyl 4-(5-(4-hexylphenyl)-pyridin-2-yl)phenyl ether

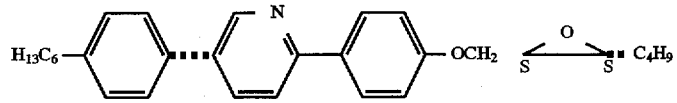

The synthesis is carried out analogously to Example 1 from hydroxy-4-[5-(4-hexylphenyl]pyridin-2-yl]benzene and (2S,3S)-3-butyloxiran-2-ylmethanol.

EXAMPLE 11

[(2S,3S)-3-Butyloxiran-2-yl]methyl 2-(4-(trans-4-propylcyclohexyl)phenyl)pyrimidin-5-yl ether

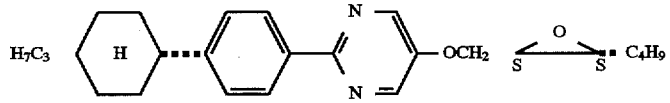

The synthesis is carried out analogously to Example 1 from 5-hydroxy-2-[4-(trans-4-propylcyclohexyl)phenyl]-pyrimidine and (2S,3S)-3-butyloxiran-2-ylmethanol.

The compound has the phase sequence:
X 114 S_c * 105 N* 188 I [α]_D²⁰=−19.97°

EXAMPLE 12

[(2S,3S)-3-Butyloxiran-2-yl]methyl 2-(4-(trans-4-pentylcyclohexylcarbonyloxy)phenyl)pyrimidin-5-yl ether

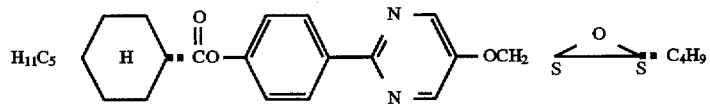

The compound has the phase sequence:
X 115 S₁ 130 S₂ 174 S₃ 198 S_c 211 S_A 222 I [α]_D²⁰=14.76°

The synthesis is carried out analogously to Example 1 from 5-hydroxy-2-[4-(trans-4-pentylcyclohexylcarbonyloxy)phenyl]pyrimidine and (2S,3S)-3-butyloxiran-2-yl-methanol.
The compound has the phase sequence:
X 103 S₁ 83 S_c * 119 N* 203 I [α]_D²⁰=−16.37°
Spontaneous polarization at 105° C.: 170 nC/cm².

EXAMPLE 13

[(2S,3S)-3-Butyloxiran-2-yl]methyl 4-(5-octyloxypyridin-2-yl)phenyl ether

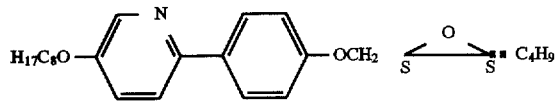

The synthesis is carried out analogously to Example 1 from 2-(4-hydroxyphenyl)-5-octyloxypyridine and (2S,3S)-3-butyloxiran-2-ylmethanol.
The compound has the phase sequence:
X 87 $S_1$ 86 $S_2$ 103 $S_4$ 111 $S_c$ * 122 I $[\alpha]_D^{20}$=−17.48°

EXAMPLE 14

[(2S,3S)-3-Butyloxiran-2-yl]methyl 4-(5-(9-decenyloxy)-pyridin-2-yl)phenyl ether

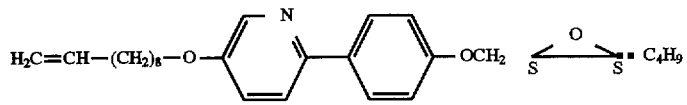

The synthesis is carried out analogously to Example 1 from 2-(4-hydroxyphenyl)-5-(7-octenyloxy)pyridine and (2S,3S)-3-butyloxiran-2-ylmethanol.
The compound has the phase sequence:
X 74 $S_1$ 70 $S_2$ 102 $S_c$ * 115 I $[\alpha]_D^{20}$=−16.95°

EXAMPLE 15

[(2S,3S)-3-Butyloxiran-2-yl]methyl 2-(4-(trans-4-pentylcyclohexlmethoxy)phenol)pyrimidin-5-yl ether

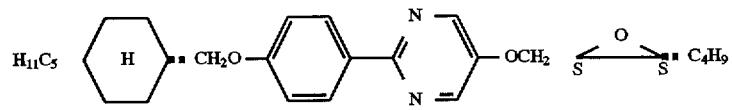

The synthesis is carried out analogously to Example 1 from 5-hydroxy-2-[4-(trans-4-pentylcyclohexylmethoxy)-phenyl]pyrimidine and (2S,3S)-3-butyloxiran-2-ylmethanol.
The compound has the phase sequence:
X 13 $S_c$ * 134 N 172 I $[\alpha]_D^{20}$=−18.36°

EXAMPLE 16

[(2S,3S)-3-Butyloxiran-2-yl]methyl 4-{5-(2S,3S)-3-propyloxiran-2-ylmethoxypyrimidin-2-yl}phenyl ether

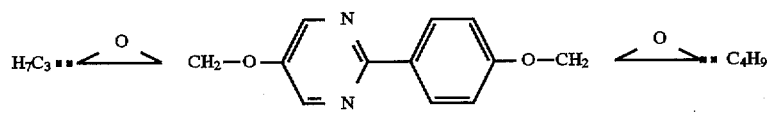

The synthesis is carried out analogously to Example 3 from [(2S,3S)-3-butyloxiran-2-yl]methyl 4-(5-hydroxypyrimidin-2-yl)phenyl ether and (2S,3S)-3-propyloxiran-2-ylmethanol.

The compound has the phase sequence:
X 101 $S_c$ * 108 N* 110 I $[\alpha]_D^{20}$=−32.5°

EXAMPLE 17

[(2S,3S)-3-Butyloxiran-2-yl]methyl 4-{5-(2S,3R)-3-propyloxiran-2-ylmethoxypyrimidin-2-yl}phenyl ether

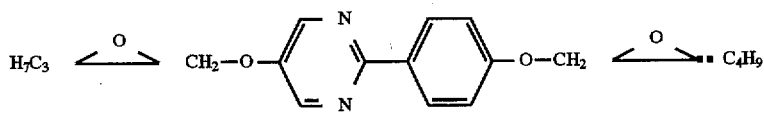

The synthesis is carried out analogously to Example 3 from [(2S,3S)-3-butyloxiran-2-yl]methyl 4-(5-hydroxypyrimidin-2-yl)phenyl ether and (2R,3R)-3-propyloxiran-2-ylmethanol.

The compound has the phase sequence:
X 79 I $[\alpha]_D = -18.0°$

EXAMPLE 18

[(2S,3S)-3-Butyloxiran-2-yl]methyl 4-{5-(4S)-2,2-dioxolan-4-ylmethoxypyrimidin-2-yl}phenyl ether

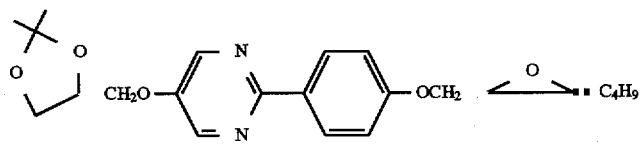

The synthesis is carried out analogously to Example 3 from [(2S,3S)-3-butyloxiran-2-yl]methyl 4-(5-hydroxypyrimidin-2-yl)phenyl ether and (S)-(+)-2,2-dimethyl-4-hydroxymethyl-1,3-dioxolane.

The compound has the phase sequence:
X 113 I $[\alpha]_D^{20} = -15.1°$

EXAMPLE 19

[(2S,3S)-3-Propyloxiran-2-yl]methyl 4-{5-(4S)-2,2-dimethyl-1,3-dioxolan-4-ylmethoxylpyrimidin-2-yl}phenyl ether

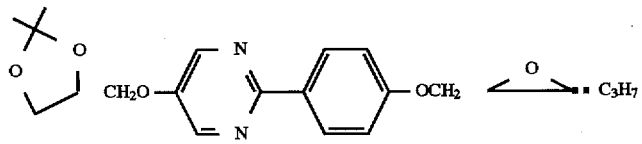

The synthesis is carried out analogously to Example 3 from [(2S,3S)-3-propyloxiran-2-yl]methyl 4-(5-hydroxypyrimidin-2-yl)phenyl ether and (S)–(+)-2,2-dimethyl-4-hydroxymethyl-1, 3-dioxolane.

The compound has the phase sequence:
X 93–120 I $[\alpha]_D^{20} = -11.7°$

EXAMPLE 20

[(2S,3S)-3-Propyloxiran-2-yl]methyl 4-{5-(2S,3S)-3-propyloxiran-2-ylmethoxypyrimidin-2-yl}phenyl ether

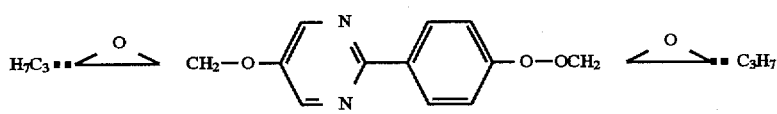

The synthesis is carried out analogously to Example 3 from [(2S,3S)-3-propyloxiran-2-yl]methyl 4-(5- hydroxypyrimidin-2-yl)phenyl ether and (2S,3S)-3-propyloxiran-2-ylmethanol.

The compound has the phase sequence:

X 112 (94) $S_A$ 102 N* 111 I $[\alpha]_D^{20}$=−37.3°

EXAMPLE 21

[(2S,3S)-3-Propyloxiran-2-yl]methyl 4-{5-(2S,3S)-3-butyloxiran-2-ylmethoxypyrimidin-2-yl}phenyl ether

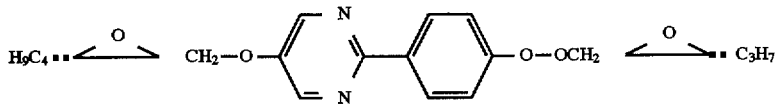

The synthesis is carried out analogously to Example 3 from [(2S,3S)-3-propyloxiran-2-yl]methyl 4-(5-hydroxypyrimidin-2-yl)phenyl ether and (2S,3S)-3-butyloxiran-2-ylmethanol.

The compound has the phase sequence:

X 99 $S_c$ * 110 I $[\alpha]_D^{20}$=−34.2°

EXAMPLE 22

[(2S,3S)-3-Propyloxiran-2-yl]methyl 4-{5-(trans-4-pentylcyclohexylcarbonyloxy)pyrimidin-2-yl}phenyl ether

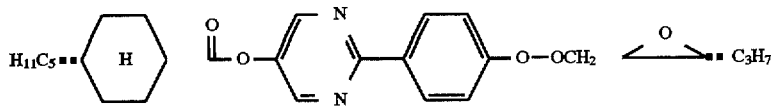

0.39 g (1.93 mmol) of dicyclohexylcarbodiimide is added to a solution of 0.5 g (1.75 mmol) of [(2S,3S)-3-propyloxiran-2-yl]methyl 4-(5-hydroxypyrimidin-2-yl)phenyl ether, 0.38 g (1.93 mmol) of trans-4-pentylcyclohexylcarboxylic acid and 0.023 g (0.193 mmol) of 4-dimethylaminopyridine in 30 ml of dichloromethane, and the mixture is stirred at room temperature for 18 hours. The reaction mixture is filtered and evaporated. The product is purified by chromatography (silica gel, CH$_2$Cl$_2$:ethyl acetate=20:1) and by recrystallization from n-heptane.

0.51 g of [(2S,3S)-3-propyloxiran-2-yl]methyl 5-{4-trans-4-pentylcyclohexylcarbonyloxy)pyrimidin-2-yl}phenyl ether is obtained.

The compound has the phase sequence:

X 105 (68) $S_A$ 181 N* 219 I $[\alpha]_D^{20}$=−14.7°

EXAMPLE 23

[(2S)-2-Methyloxiran-2-yl]methyl 4-{5-(10-undecenyloxy)-pyrimidin-2-yl}phenyl ether

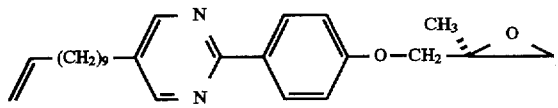

The synthesis is carried out analogously to Example 3 from [(2S)-2-methyloxiran-2-yl]methyl 4-(5-hydroxypyrimidin-2-yl)phenyl ether and 10-undecen-1-ol.

The compound has the phase sequence:

X 63 $S_c$ * 46 $S_A$ 66 I $[\alpha]_D^{20}$=+1.78°

EXAMPLE 24

[(2R)-2-Methyloxiran-2-yl]methyl 4-{5-(10-undecenyloxy)-pyrimidin-2-yl}phenyl ether

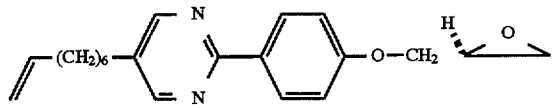

The synthesis is carried out analogously to Example 3 from [(2R)-2-methyloxiran-2-yl]methyl 4-(5-hydroxypyrimidin-2-yl)phenyl ether and 10-undecen-1-ol.

The compound has the phase sequence:

X 63 $S_c$ * 46 $S_A$ 66 I $[\alpha]_D^{20}$=−1.63°

EXAMPLE 25

[(2S)-2-Oxiran-2-yl]methyl 4-{5-(7-octenyloxy)pyrimidin-2-yl}phenyl ether

The synthesis is carried out analogously to Example 3 from [(2S)-2-oxiran-2-yl]methyl 4-(5-hydroxypyrimidin-2-yl)phenyl ether and 7-undecen-1-ol.

The compound has the phase sequence:

X 62 $S_A$ 69 N* 72 I $[\alpha]_D^{20}$=+3.5°

EXAMPLE 26

[(2S,3S)-3-Butyloxiran-2-yl]methyl 4-{5-(2R)-2-methyloxiran-2-ylmethoxypyrimidin-2-yl}phenyl ether

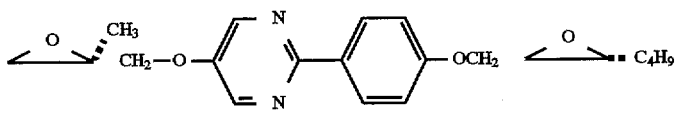

The synthesis is carried out analogously to Example 3 from [(2S,3S)-3-butyloxiran-2-yl]methyl 4-(5-hydroxypyrimidin-2-yl)phenyl ether and (2S)-2-methyloxiran-2-ylmethanol.

The compound has the phase sequence:
X 112 I $[\alpha]_D^{20}=-18.5°$

EXAMPLE 27

5-Oxanonyl 4-{5-(2S)-2-methyloxiran-2-ylmethoxypyrimidin-2-yl}phenyl ether

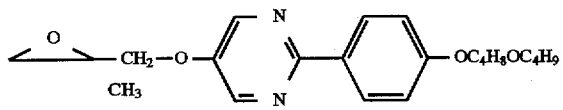

The synthesis is carried out analogously to Example 3 from 5-oxanonyl 4-(5-hydroxypyrimidin-2-yl)phenyl ether and (2R)-2-methyloxiran-2-ylmethanol.
The compound has the phase sequence:
X53I $[\alpha]_D^{20}=-1.7°$

EXAMPLE 28

5-Oxanonyl 4-{5-(2S)-2-methoxypyrimidin-2-yl}phenyl ether

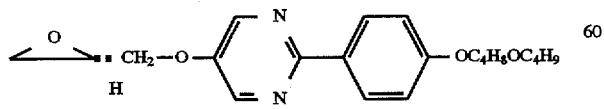

The synthesis is carried out enalogously to Example 3 from 5-oxanonyl 4-(5-hydroxypyrimidin-2-yl)phenyl ether and (2R)-2-oxiranylmethanol.

The compound has the phase sequence:
X 62 I $[\alpha]_D^{20}=+4.7°$

EXAMPLE 29

5-Oxanonyl 4-{5-(2S,3S)-3-propyloxiran-2-ylmethoxypyrimidin-2-yl}phenyl ether

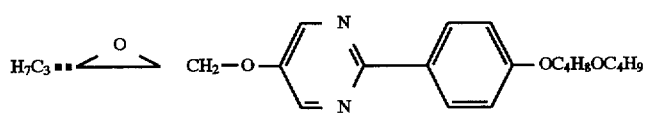

The synthesis is carried out enalogously to Example 3 from 5-oxanonyl 4-(5-hydroxypyrimidin-2-yl)phenyl ether and (2S,3S)-3-propyloxiran-2-ylmethanol.
The compound has the phase sequence:
X 60 $S_c$ * 85 $S_A$ 90 I $[\alpha]_D^{20}=-16.6°$

EXAMPLE 30

5-Oxanonyl 4-{5-(2S,3S)-3-butyloxiran-2-ylmethoxypyrimidin-2-yl}phenyl ether

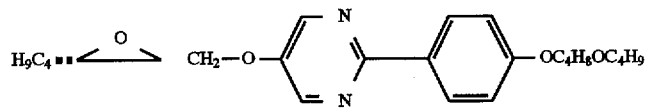

The synthesis is carried out analogously to Example 3 from 5-oxanonyl 4-(5-hydroxypyrimidin-2-yl)phenyl ether and (2S,3S)-3-butyloxiran-2-ylmethanol.

The compound has the phase sequence:
X 56 $S_c$ * 91 I $[\alpha]_D^{20}=-19.9°$

EXAMPLE 31

[(2S,3S)-3-Propyloxiran-2-yl]methyl 2-{4-(trans-4-pentylcyclohexylcarbonyloxy)pyrimidin-5-yl}phenyl ether

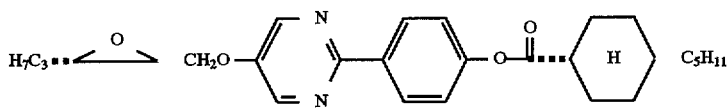

The synthesis is carried out analogously to Example 1 from 5-hydroxy-2-[4-(trans-4-pentylcyclohexylcarbonyloxy) phenyl]pyrimidine and (2S,3S)-3-propyloxiran-2-yl-methanol.

The compound has the phase sequence:

X 129 N.* 214 I $[\alpha]_D^{20} = -16.8°$

EXAMPLE 32

[(2R)-2-Methyloxiran-2-yl]methyl 4-{5-(4-hexylphenyl)-pyrimidin-2-yl}phenyl ether

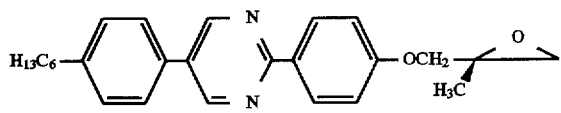

The synthesis is carried out analogously to Example 1 from 5-(4-hexylphenyl)-2-(4-hydroxyphenyl)pyrimidine and (2S)-2-methyloxiran-2-ylmethanol.

The compound has the phase sequence:

X 106 $S_3$ 115 $S_2$ 122–126 $S_A$ 180 I $[\alpha]_D^{20} = -1.12°$

EXAMPLE 33

[(2S)-2-Methyloxiran-2-yl]methyl 4-{5-(4-hexylphenyl)-pyrimidin-2-yl}phenyl ether

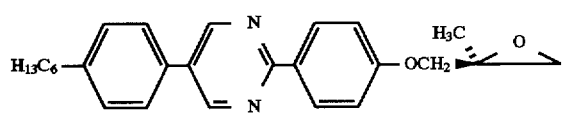

The synthesis is carried out analogously to Example 1 from 5-(4-hexylphenyl)-2-(4-hydroxyphenyl)pyrimidine and (2R)-2-methyloxiran-2-ylmethanol.

The compound has the phase sequence:

X 106 $S_3$ 115 $S_2$ 122–126 $S_A$ 180 I $[\alpha]_D^{20} = -1.04°$

EXAMPLE 34

[(2S,3S)-3-Butyloxiran-2-yl]methyl 4-{5-(2S)-2-methyloxiran-2-ylcarbonyloxypyrimidin-2-yl}phenyl ether

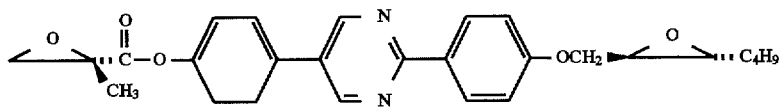

The synthesis is carried out analogously to Example 22 from [(2S,3S)-3-butyloxiran-2-yl]methyl 4-(5-hydroxypyrimidin-2-yl)phenyl ether and (2S)-2-methyloxiran-2-ylcarboxylic acid.

The compound has the phase sequence:

X 91 N* 65 I $[\alpha]_D^{20} = -1.04°$

EXAMPLE 35

[(2S,3S)-3-Butyloxiran-2-yl]methyl 4-(2-dodecyloxypyridin-5-yl) phenyl ether

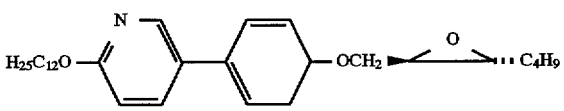

The synthesis is carried out analogously to Example 1 from 5-(4-hydroxyphenyl)-2-dodecyloxypyridine and (2S,3S)-3-butyloxiran-2-ylmethanol.

The compound has the following phase sequence:

X 42 $S_c$ * 90 $S_A$ 97 I $[\alpha]_D^{20} = -13.6°$

EXAMPLE 36

[(2S,3S)-3-Butyloxiran-2-yl]methyl 4-(2-hexyloxypyridin-5-yl)phenyl ether

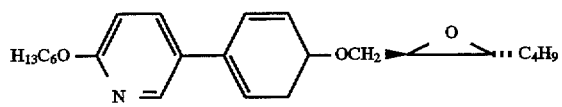

The synthesis is carried out analogously to Example 1 from 5-(4-hydroxyphenyl)-2-hexylpyridine and (2S,3S)-3-butyloxiran-2-yl)methanol.

The compound has the following phase sequence:

$X_1$ B (−24) $X_2$ 38 $S_c$ * 92 $S_A$ 101 I $[\alpha]_D^{20} = -18.2°$

Use Example 1 a) A ferroelectric mixture comprising the components

| | |
|---|---|
| 5-octyloxy-2-(4-hexyloxyphenyl)pyrimidine | 22.8 mol-% |
| 5-octyloxy-2-(4-butoxyphenyl)pyrimidine | 24 mol-% |
| 5-octyloxy-2-(4-decyloxyphenyl)pyrimidine | 19.2 mol-% |
| 5-octyloxy-2-(4-octyloxyphenylpyrimidine | 10.5 mol-% |
| 4'-(5-decylpyrimidin-2-yl)phenyl trans-4-pentylcyclohexanecarboxylate | 13.5 mol-% |
| ((2S,3S)-3-butyloxiran-2-yl)methyl 4-(5-(4-hexylphenyl)pyrimidin-2-yl)phenyl ether | 10 mol-% | has the following liquid-crystalline phase ranges:

$S_c$ * 88 $S_A$ 100 N 120 I and has a spontaneous polarization of 16.6 nC/cm$^2$ at a temperature of 20° C. and switches with a response time of 180 µs at a field strength of 10 V/µm.

Use Example 2 a) A ferroelectric mixture comprising the components

| | |
|---|---|
| 5-octyloxy-2-(4-hexyloxyphenyl)pyrimidine | 24.1 mol-% |
| 5-octyloxy-2-(4-butoxyphenyl)pyrimidine | 25.4 mol-% |
| 5-octyloxy-2-(4-decyloxyphenyl)pyrimidine | 20.2 mol-% |
| 5-octyloxy-2-(4-octyloxyphenyl)pyrimidine | 11.1 mol-% |
| 4'-(5-decylpyrimidin-2-yl)phenyl trans-4-pentylcyclohexanecarboxylate | 14.3 mol-% |
| ((2S,3S)-3-butyloxiran-2-yl)methyl 4-(4-(5-octylpyrimidin-2-yl)phenyl)phenyl ether | 5 mol-% | has the following liquid-crystalline phase ranges:

$S_c$ * 87 $S_A$ 94 N 108 I and has a spontaneous polarization of 5.0 nC/cm$^2$ at a temperature of 20° C.

By comparison, the liquid-crystalline mixture claimed in DE 38 31 226, which differs from the abovementioned mixtures only in that it does not contain a dopant, has the following phase ranges:

$S_c$ * 84 $S_A$ 93 N 105 I

The addition of the dopants induces a polarization and also increases all the liquid-crystalline phase transitions.

Use Example 3 a) A ferroelectric mixture comprising the components

| | |
|---|---|
| 5-octyl-2-(4-hexyloxyphenyl)pyrimidine | 14.2 mol-% |
| 5-octyl-2-(4-decyloxyphenyl)pyrimidine | 9.5 mol-% |
| 5-decyl-2-(4-hexyloxyphenyl)pyrimidine | 9.2 mol-% |
| 5-octyl-2-(4-(7-cyclopropylheptyloxy)phenyl)pyridine | 7.7 mol-% |
| 5-octyl-2-(4-(6-cyclopropyl)hexylcarbonyloxyphenyl)pyrimidine | 9.6 mol-% |
| 5-(8-cyclopropyloctyloxy)-2-(4-trans-pentylcyclohexyl-4-phenyl)pyrimidine | 11.0 mol-% |
| 4-(8-cyclopropyloctyl)pyrimidin-2-yl-phenyl trans-4-pentylcyclohexanecarboxylate | 6.8 mol-% |
| 5-(5-cyclopropylpentyloxy-2-(4-hexyloxyphenyl)pyrimidine | 10.2 mol-% |
| 2-(4-hexylphenyl)-5-(4-(4-cyclopropylbutoxyphenyl)pyrimidine | 6.8 mol-% |
| ((2S,3S)-3-butyloxiran-2-yl)methyl 4-(5-(4-hexylphenyl)pyrimidin-2-yl)phenyl ether | 15.0 mol-% | has the following liquid-crystalline phase ranges:

$S_c$ * 78.8 $S_A$ 89.5 N* 108.2 I

It has a helical twisting power of 1.47/µm at a temperature of 90°. By comparison, the liquid-crystalline mixture which differs from the abovementioned mixture only in that it does not contain an oxirane dopant has the following phase ranges:

$S_c$ 67.5 $S_A$ 77.3 N 94.8 I

The addition of the compound according to the invention, in addition to forming a helix which can be utilized in mixtures for compensating the helical twist, results in an increase in all the liquid-crystalline phase ranges.

Use Examples 4 to 29 below (Table 1) were carried out using base mixture A.

Mixture A:

| | |
|---|---|
| 5-octyloxy-2-(4-hexyloxyphenyl)pyrimidine | 25.34 mol-% |
| 5-octyloxy-2-(4-octyloxyphenyl)pyrimidine | 11.69 mol-% |
| 5-octyloxy-2-(4-butoxyphenyl)pyrimidine | 26.73 mol-% |
| 5-octyloxy-2-(4-decyloxyphenyl)pyrimidine | 21.24 mol-% |
| 4'-(5-decylpyrimidin-2-yl)phenyl trans-4-pentylcyclohexanecarboxylate | 15 mol-% |

TABLE 1

Dopants according to the invention in base mixture A

| Use Example | Substance Example | A: Substance Example mixing ratio | Measurement temperature [°C.] | $P_s$ [nC/c-m$^2$] | Response time [µs] |
|---|---|---|---|---|---|
| 4 | 3 | 90:10 | 20 | 49 | |
| 5 | 4 | 90:10 | 20 | 4 | 370 |
| 6 | 5 | 90:10 | 20 | 15 | |
| 7 | 6 | 90:10 | 20 | 43 | |
| 8 | 8 | 90:10 | 20 | 15 | |
| 9 | 10 | 90:10 | 20 | 11 | |
| 10 | 11 | 90:10 | 25 | 13 | 230 |
| 11 | 12 | 90:10 | 20 | 49 | |
| 12 | 14 | 90:10 | 20 | 8 | 312 |
| 13 | 15 | 90:10 | 20 | 16 | 180 |
| 14 | 16 | 90:10 | 20 | 20 | |
| 15 | 17 | 90:10 | 20 | 74 | |
| 16 | 18 | 90:10 | 40 | 11.5 | |
| 17 | 19 | 90:10 | 20 | 14.5 | |
| 18 | 20 | 90:10 | 20 | 19 | |
| 19 | 21 | 90:10 | 20 | 24 | |
| 20 | 22 | 90:10 | 20 | 7.5 | |

TABLE 1-continued

Dopants according to the invention in base mixture A

| Use Example | Substance Example | A: Substance Example mixing ratio | Measurement temperature [°C.] | $P_s$ [nC/c-m$^2$] | Response time [µs] |
|---|---|---|---|---|---|
| 21 | 23 | 90:10 | 20 | 5.5 | |
| 22 | 24 | 90:10 | 20 | 4.5 | |
| 23 | 25 | 90:10 | 20 | 4 | |
| 24 | 26 | 90:10 | 40 | 1.2 | |
| 25 | 27 | 90:10 | 20 | 8.5 | 300 |
| 26 | 29 | 90:10 | 20 | 8.4 | |
| 27 | 30 | 90:10 | 20 | 13.5 | |
| 28 | 31 | 90:10 | 20 | 21 | |
| 29 | 33 | 90:10 | 20 | 5.5 | |

Addition of the compounds claimed according to the invention to an achiral base mixture A induces high spontaneous polarization. The resultant ferroelectric mixtures are capable of bistable switching and can thus be used in suitable combinations in the display.

In addition, dopants according to the invention were tested in base mixture B (Use Examples 30 to 52, Table 2).

Mixture B:

| | |
|---|---|
| 5-octyloxy-2-(4-hexyloxyphenyl)pyrimidine | 11.06 mol-% |
| 5-octyloxy-2-(4-octyloxyphenyl)pyrimidine | 5.11 mol-% |
| 5-octyloxy-2-(4-butoxyphenyl)pyrimidine | 11.67 mol-% |
| 5-octyloxy-2-(4-decyloxyphenyl)pyrimidine | 9.28 mol-% |
| 5-octyl-2-(4-octyloxyphenyl)pyridimidine | 15.88 mol-% |
| 5-octyl-2-(4-hexyloxyphenyl)pyrimidine | 17.7 mol-% |
| 5-octyl-2-(4-decyloxyphenyl)pyrimidine | 11.8 mol-% |
| 4'-(5-dodecylpyrimidin-2-yl)phenyl trans-4-pentylcyclohexanecarboxylate | 17.5 mol-% |

Mixture B has the following liquid-crystalline phase ranges:

$S_c$ 69 $S_A$ 76 N 94 I

In addition to the induction of spontaneous polarization, it is evident from the above table that the compounds claimed according to the invention raise the $S_c*/S_A*$ transition compared with the achiral mixture B and thus broaden the practicable temperature range.

The helical twisting power of these compounds can advantageously be used to increase the twisting in the cholesteric phase.

A sufficiently large pitch in the helix in the cholesteric phase is necessary in order to achieve good homogeneous alignment of the liquid-crystal mixture in displays.

In Use Examples 53 and 54, the critical pulse area of ferroelectric mixtures containing dopants according to the invention was determined. The critical pulse area is taken to mean the product of the critical pulse width and the field strength used.

The critical pulse width is the minimum pulse width necessary to switch the FLC from one stable switching state to another. It is determined by first switching the FLC into one of the two stable switching states by means of a sufficiently large bipolar resetting pulse and, after 20 ms, using an inverse bipolar pulse whose width is varied until switching takes place.

TABLE 2

Dopants according to the invention in base mixture B

| Invention Example | Substance Example | B: Substance Example mixing ratio | Measurement temperature [°C.] | HTP [µm$^{-1}$] | Liquid-crystalline phase ranges of the test mixture |
|---|---|---|---|---|---|
| 30 | 3 | 90:8 | 80 | −2.27 | S*$_c$ 73 S$_A$ 78 N* 94 I |
| 31 | 4 | 90:10 | 80 | −0.56 | S*$_c$ 71.50 S$_A$ 78 N* 94.5 I |
| 32 | 5 | 90:10 | 81 | −0.5 | S*$_c$ 75 S$_A$ 79 N* 98 I |
| 33 | 6 | 95:5 | 74 | −3.75 | S*$_c$ 65.50 S$_A$ 72 N* 94 I |
| 34 | 7 | 95:5 | 80 | −0.84 | S*$_c$ 73 S$_A$ 78 N* 94 I |
| 35 | 8 | 95:5 | 82 | −2.3 | S*$_c$ 69 S$_A$ 80 N* 97 I |
| 36 | 9 | 90:10 | 82 | −0.75 | S*$_c$ 76 S$_A$ 80 N* 102 I |
| 37 | 10 | 95:5 | 84 | −1.73 | S*$_c$ 74 S$_A$ 82 N* 99 I |
| 38 | 11 | 90:10 | 81 | −0.6 | S*$_c$ 75 S$_A$ 79 N* 101 I |
| 39 | 12 | 95:5 | 79 | −1.39 | S*$_c$ 68 S$_A$ 77 N* 87 I |
| 40 | 15 | 95:5 | 78 | −0.78 | S*$_c$ 74 S$_A$ 76 N* 98 I |
| 41 | 16 | 90:10 | 80 | −2.47 | S*$_c$ 73 S$_A$ 78 N* 95 I |
| 42 | 17 | 90:10 | 62 | −8.5 | S*$_c$ 60 N* 87 I |
| 43 | 18 | 90:10 | 68 | −0.85 | S*$_c$ 66 N* 90 I |
| 44 | 19 | 95:5 | 72 | −1.4 | S*$_c$ 67 S$_A$ 70 N* 91 I |
| 45 | 21 | 90:10 | 79 | −1.49 | S*$_c$ 73 S$_A$ 77 N* 95 I |
| 46 | 22 | 90:10 | 62 | −1.04 | S*$_c$ 70 S$_A$ 80 N* 104 I |
| 47 | 26 | 92:8 | 73 | −1.33 | S*$_c$ 66 S$_A$ 71 N* 91 I |
| 48 | 27 | 90:10 | 63 | 0.26 | S*$_c$ 61 N* 87.5 I |
| 49 | 28 | 90:10 | 75 | 1.1 | S*$_c$ 64 S$_A$ 73 N* 91 I |
| 50 | 29 | 90:10 | 80 | 0.6 | S*$_c$ 71 S$_A$ 78 N* 93 I |
| 51 | 31 | 90:10 | 74 | −0.28 | S*$_c$ 72 N* 105 I |
| 52 | 34 | 95:5 | 69 | −6.32 | S*$_c$ 67 N* 92 I |

In the two examples below, the critical pulse area was determined by applying bipolar pulses having a pulse width of 30 μs and measuring the pulse area of a side.

Use Example 53

A ferroelectric mixture comprising the components

| | |
|---|---|
| 5-octyl-2-(4-hexyloxyphenyl)pyrimidine | 16.1 mol-% |
| 5-octyl-2-(4-decyloxyphenyl)pyrimidine | 10.7 mol-% |
| 5-octyl-2-(4-octyloxyphenyl)pyrimidine | 14.5 mol-% |
| 5-octyloxy-2-(4-hexyloxyphenyl)pyrimidine | 10 mol-% |
| 5-octyloxy-2-(4-octyloxyphenyl)pyrimidine | 4.6 mol-% |
| 5-octyloxy-2-(4-butoxyphenyl)pyrimidine | 10.5 mol-% |
| 5-octyloxy-2-(4-decyloxyphenyl)pyrimidine | 8.4 mol-% |
| 4-(5-[10-undecenyloxy})pyrimidin-2-yl-phenyl (2R,3R)-3-propyloxirane-2-carboxylate | 6 mol-% |
| [(2S,3S)-3-butyloxiran-2-yl]methyl 2-(4-(trans-4-pentylcyclohexylcarbonyloxy)-phenyl)pyrimidin-5-yl ether | 9.6 mol-% |
| [(2S,3S)-3-butyloxiran-2-yl]methyl 4-(5-(4-hexylphenyl)pyrimidin-2-yl)phenyl ether | 9.6 mol-% | has the following liquid-crystalline phase ranges:

S*$_c$ 74 S$_A$ 87 N* 98 I and has a spontaneous polarization of 53 nC/cm² at a temperature of 25° C.

The mixture switches at 25° C. with a critical pulse area of 630 Vs/m.

The helical twisting is substantially increased over the entire temperature range of the cholesteric phase.

The same mixture without the compounds according to the invention has the following liquid-crystalline phase ranges:

S*$_c$ 56 S$_A$ 77 N* 79 I and has a spontaneous polarization of 12 nC/cm² at 25° C. The helical twisting power is +4.9 μm⁻¹ at 18° C.

It is clearly evident from the above comparison that the compounds claimed here not only broaden the practical phase range and substantially increase the helical twisting, but also considerably increase the spontaneous polarization and thus shorten the response times.

Use Example 54

A ferroelectric mixture comprising the components

| | |
|---|---|
| 5-octyl-2-(4-hexyloxyphenyl)pyrimidine | 17.1 mol-% |
| 5-octyl-2-(4-decyloxyphenyl)pyrimidine | 11.4 mol-% |
| 5-octyl-2-(4-octyloxyphenyl)pyrimidine | 15.3 mol-% |
| 5-octyloxy-2-(4-hexyloxyphenyl)pyrimidine | 10.7 mol-% |
| 5-octyloxy-2-(4-octyloxyphenyl)pyrimidine | 4.9 mol-% |
| 5-octyloxy-2-(4-butoxyphenyl)pyrimidine | 11.2 mol-% |
| 5-octyloxy-2-(4-decyloxyphenyl)pyrimidine | 8.9 mol-% |
| 4-(5-[10-undecenyloxy})pyrimidin-2-yl-phenyl (2R,3R)-3-propyloxirane-2-carboxylate | 5.5 mol-% |
| [(2S,3S)-3-butyloxiran-2-yl]methyl 2-(4-(trans-4-pentylcyclohexylcarbonyloxy)-phenyl)pyrimidin-5-yl ether | 7 mol-% |
| [(2S,3S)-3-butyloxiran-2-yl]methyl 4-{5-(2S,3S)-3-butyloxiran-2-ylmethoxypyrimidin-2-yl}phenyl ether | 8 mol-% | has the following liquid-crystalline phase ranges:

S*$_c$ 69 S$_A$ 80 N* 87 I and has a spontaneous polarization of 47 nC/cm² at a temperature of 25° C.

The mixture switches at 25° C. with a critical pulse area of 670 Vs/m.

The helical twisting is substantially increased over the entire temperature range of the cholesteric phase.

We claim:

1. A liquid-crystal mixture which contains from 0.01 to 60% by weight of at least one oxiranylmethyl ether of the formula (I)

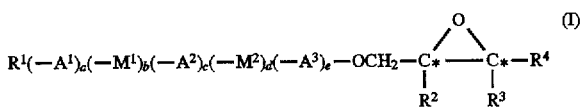

in which the symbols and indices have the following meanings:

* is a center of chirality, $R^1$ is a straight-chain or branched alkyl radical having 1 to 16 carbon atoms (with or without an asymmetric carbon atom), it also being possible for one or more non-adjacent —$CH_2$— groups to be replaced by —O—, —CO—, —CO—O—, —O—CO—, —O—CO—O—, —CH=CH—, —C≡C— or Δ, and/or for one or more H atoms of the alkyl radical to be substituted by F or is one of the following chiral groups:

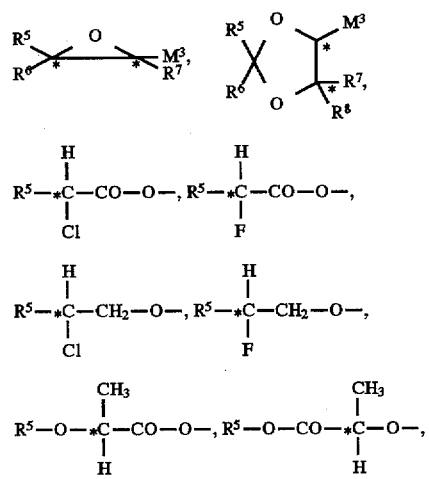

$R^2$, $R^3$, $R^4$, $R^5$, $R^6$, $R^7$ and $R^8$, independently of one another, are H or a straight-chain or branched alkyl radical having 1 to 16 carbon atoms, or $R^5$ and $R^6$ together may alternatively be —$(CH_2)_4$— or —$(CH_2)_5$— if they are bonded as substituents to a dioxolane system, $A^1$, $A^2$ and $A^3$ are identical or different and are 1,4-phenylene, in which one or two H atoms may be replaced by F and/or CN, pyrazine-2,5-diyl, pyridine-2,5-diyl, pyrimidine-2,5-diyl, trans-1,4-cyclohexylene, in which one H atom may be replaced by CN, 1,3,4-thiadiazole-2,5-diyl, 1,3-dioxane-2,5-diyl, 1,3-thiazole-2,4-diyl, 1,3-thiazole-2,5-diyl, thiophene-2,4-diyl, thiophene-2,5-diyl or naphthalene-2,6-diyl, where $A^1$ and $A^2$ and $A^3$ cannot simultaneously be unsubstituted 1,4-phenylene if $M^1$ or $M^2$ is —COO—, $M^1$ and $M^2$ are identical or different and are —CO—O—, —O—CO—, —O—CO—O—, —$CH_2$—O—, —O—$CH_2$—, —$CH_2CH_2$—, —CH=CH— or —C≡C—, $M^3$ is —$CH_2$—O—, —O—$CH_2$—, —CO—O—, —O—CO— or a single bond, a, b, c, d and e are zero or one, with the proviso that the sum a+c+e is 1, 2 or 3, with the exception of the compounds in which the (—$A^1$)$_a$(—$M^1$)$_b$(—$A^2$)$_c$(—$M^2$)$_d$(—$A^3$)$_e$-group has the following meanings:

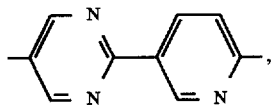

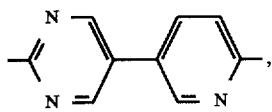

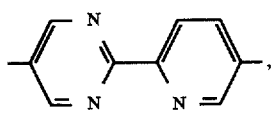

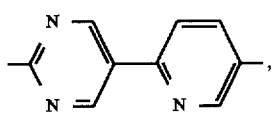

and with the exception of the compounds in which the $R^1(-A^1)_a(M^1)_b(-A^2)_c(-M^2)_d(-A^3)_e-$ group has the following meanings:

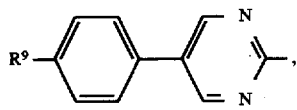

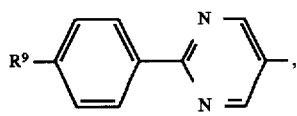

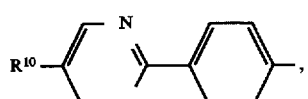

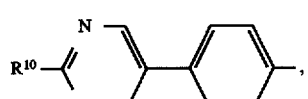

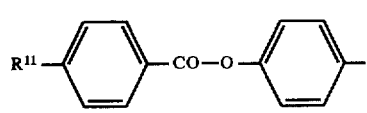

where
$R^9$ is straight-chain or branched ($C_3$–$C_{12}$)-alkenyl containing a terminal double bond, in which one or two non-adjacent $CH_2$ groups may be replaced by O and/or S atoms, $R^{10}$ is straight-chain or branched alkyl having 1–12 carbon atoms, in which one or two non-adjacent $CH_2$ groups may be replaced by O and/or S atoms, and $R^{11}$ is an alkoxy group having 5–12 carbon atoms,

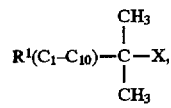

where
X is straight-chain or branched alkylene having 1 to 16 carbon atoms, in which one or two non-adjacent —$CH_2$— groups may also be replaced by —O—, —S—, —O—CO—, —CO—O—, —CO— or —O—CO—O—.

2. A chiral oxiranylmethyl ether of the formula (I)

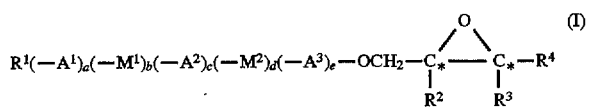

in which the symbols and indices have the following meanings:

* is a center of chirality, $R^1$ is a straight-chain or branched alkyl radical having 1 to 16 carbon atoms (with or without an asymmetric carbon atom), it also being possible for one or more non-adjacent —$CH_2$— groups to be replaced by —O—, —CO—, —CO—O—, —O—CO—, —O—CO—O—, —CH=CH—, —C≡C— or Δ, and/ or for one or more H atoms of the alkyl radical to be substituted by F, or is one of the following chiral groups:

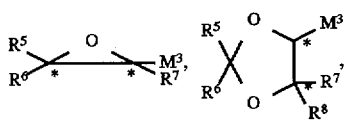

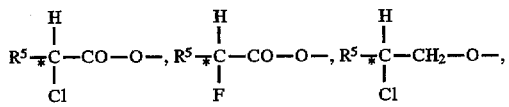

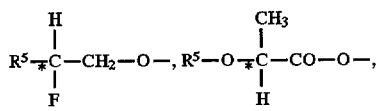

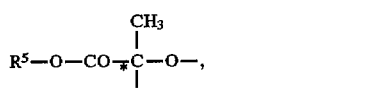

$R^2$, $R^3$, $R^5$, $R^6$, $R^7$ and $R^8$, independently of one another, are H or a straight-chain or branched alkyl radical having 1 to 16 carbon atoms, or $R^5$ and $R^6$ together may alternatively be —$(CH_2)_4$— or —$(CH_2)_5$— if they are bonded as substituents to a dioxolane system, $R^4$ is a straight-chain or branched alkyl radical having 1 to 16 carbon atoms, $A^1$, $A^2$ and $A^3$ are identical or different and are 1,4-phenylene, in which one or two H atoms may be replaced by F and/or CN, pyrazine-2,5-diyl, pyridine-2,5-diyl, pyrimidine-2,5-diyl, trans-1,4-cyclohexylene, in which one H atom may be replaced by CN, 1,3,4-thiadiazole-2,5-diyl, 1,3-dioxane-2,5-diyl, 1,3-thiazole-2,4-diyl, 1,3-thiazole-2,5-diyl, thiophene-2,4-diyl, thiophene-2,5-diyl or naphthalene-2,6-diyl, where $A^1$ and $A^2$ and $A^3$ cannot simultaneously be unsubstituted 1,4-phenylene if $M^1$ or $M^2$ is —COO—, $M^1$ and $M^2$ are identical or different and are —CO—O—, —O—CO—, —O—CO—O—, —$CH_2$—O—, —$CH_2$—, —$CH_2CH_2$—, —CH=CH— or —C≡C—, $M^3$ is —$CH_2$—O—, —O—$CH_2$—, —CO—O—, —O—CO— or a single bond, a, b, c, d and e are zero or one, with the proviso that the sum a+c+e is 1, 2 or 3, with the exception of the compounds in which the $(-A^1)_a(-M^1)_b(-A^2)_c(-M^2)_d(-A^3)_e-$ group has the following meanings:

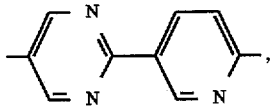

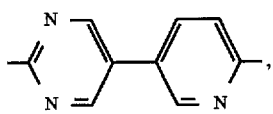

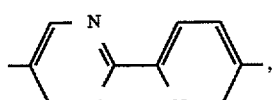

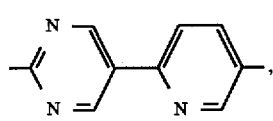

and with the exception of the compounds in which the $R^1(-A^1)_a(-M^1)_b(-A^2)_c(M^2)_d(-A^3)_e-$ group has the following meanings:

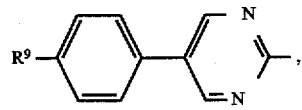

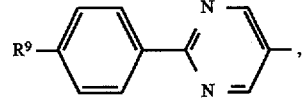

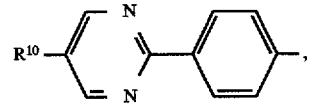

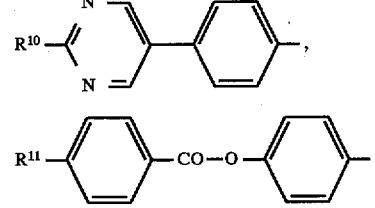

where $R^9$ is straight-chain or branched $(C_3-C_{12})$-alkenyl containing a terminal double bond, in which one or two non-adjacent $CH_2$ groups may be replaced by O and/or S atoms, $R^{10}$ is straight-chain or branched alkyl having 1–12 carbon atoms, in which one or two non-adjacent $CH_2$ groups may be replaced by O and/or S atoms, and $R^{11}$ is an alkoxy group having 5–12 carbon atoms,

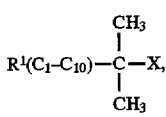

where

X is straight-chain or branched alkylene having 1 to 16 carbon atoms in which one or two non-adjacent $-CH_2-$ groups may also be replaced by $-O-$, $-S-$, $-O-CO-$, $-CO-O-$, $-CO-$ or $-O-CO-O-$.

3. A chiral oxiranylmethyl ether as claimed in claim 2, wherein the symbols and indices in the formula (I) have the following meanings:

$R^1$ is a straight-chain or branched alkyl radical having 1 to 16 carbon atoms (with or without an asymmetric carbon atom), it also being possible for one or more $-CH_2-$ groups to be replaced by $-O-$, $-CO-$, $-CO-O-$, $-O-CO-$, $-O-CO-O$, $-CH=CH-$, $-C≡C-$ or Δ, or is one of the following chiral groups:

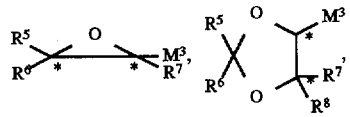

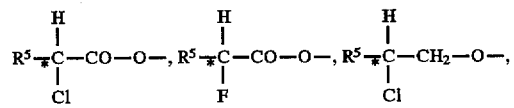

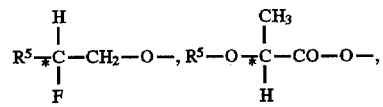

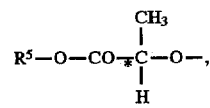

$R^2$, $R^3$, $R^5$, $R^6$, $R^7$ and $R^8$, independently of one another, are H or a straight-chain or branched alkyl radical having 1 to 16 carbon atoms, where $R^5$ and $R^6$ together may alternatively be $-(CH_2)_4-$ or $-(CH_2)_5-$ if they are bonded as substituents to a dioxolane system, $R^4$ is a straight-chain or branched alkyl radical having 1 to 16 carbon atoms, $A^1$, $A^2$ and $A^3$ are identical or different and are 1,4-phenylene, pyrazine-2,5-diyl, pyridine-2,5-diyl, pyrimidine-2,5-diyl, trans-1,4-cyclohexylene, 1,3,4-thiadiazole-2,5-diyl, 1,3-dioxane-2,5-diyl or naphthalene-2,6-diyl, where $A^1$ and $A^2$ and $A^3$ cannot simultaneously be unsubstituted 1,4-phenylene if $M^1$ or $M^2$ is $-COO-$, $M^1$ and $M^2$ are identical or different and are $-CO-O-$, $-O-CO-$, $-CH_2-O-$, $-O-CH_2-$, $-CH_2-CH_2-$, $-CH=CH-$ or $-C≡C-$, and $M^3$ is $-CH_2-O-$, $-O-CH_2-$, $-CO-O-$, $-O-CO-$ or a single bond.

4. A chiral oxiranylmethyl ether as claimed in claim 2, wherein the symbols and indices in the formula (I) have the following meanings:

$R^1$ is a straight-chain or branched alkyl radical having 1 to 16 carbon atoms (with or without an asymmetric carbon atom), it also being possible for one or two —CH₂— groups to be replaced by —O—, —CO—, —CO—O—, —O—CO—, —CH=CH—, or Δ, or is one of the following chiral groups:

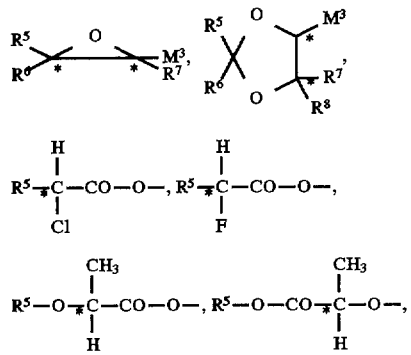

R², R³, R⁵, R⁶, R⁷ and R⁸, independently of one another, are H or a straight-chain or branched alkyl radical having 1 to 16 carbon atoms, where R⁵ and R⁶ together may alternatively be —(CH₂)₄— or —(CH₂)₅— if they are bonded as substituents to a dioxolane system, R⁴ is a straight-chain or branched alkyl radical having 1 to 16 carbon atoms, A¹, A² and A³ are identical or different and are 1,4-phenylene, pyrazine-2,5-diyl, pyridine-2,5-diyl, pyrimidine-2,5-diyl, trans-1,4-cyclohexylene, 1,3,4-thiadiazole-2,5-diyl or naphthalene-2,6-diyl, where A¹ and A² and A³ cannot simultaneously be unsubstituted 1,4-phenylene if M¹ or M² is —COO—, M¹ and M² are identical or different and are —CO—O—, —O—CO—, —CH₂—O—, —O—CH₂—, —CH₂CH₂—, —CH=CH— or —C≡C—, and M³ is —CH₂—O—, —O—CH₂—, —CO—O—, —O—CO— or a single bond.

5. A chiral oxiranylmethyl ether as claimed in claim 2, wherein

R¹ is an alkyl radical having 1 to 16 carbon atoms, it being possible for one or two non-adjacent —CH₂— groups to be replaced by —O—, Δ or —CH=CH—, or is one of the chiral groups

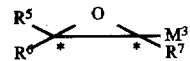

R², R³, R⁵ and R⁶, independently of one another, are H or an alkyl radical having 1 to 16 carbon atoms, R⁴ is a straight-chain or branched alkyl radical having 1 to 16 carbon atoms, M³ is —CH₂—O— or —CO—O—, and the (—A¹)ₐ(—M¹)ᵦ(—A²)꜀(—M²)ᵈ(—A³)ₑ-group has the following meanings:

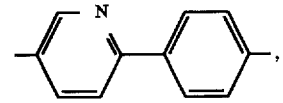

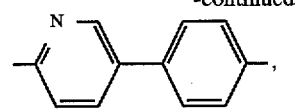

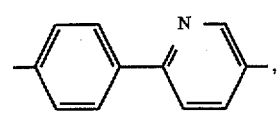

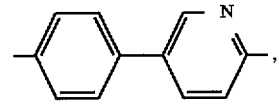

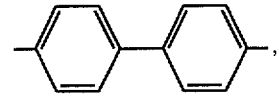

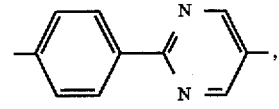

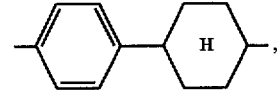

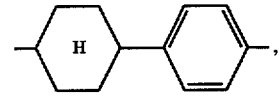

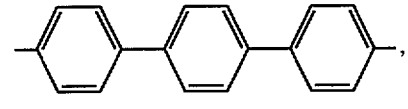

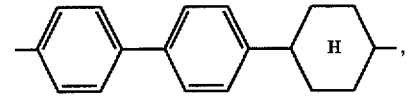

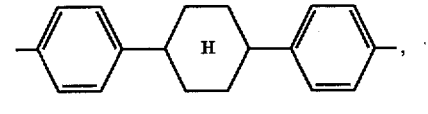

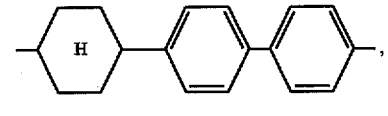

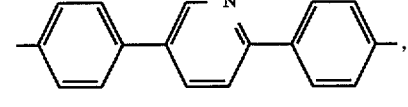

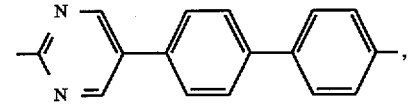

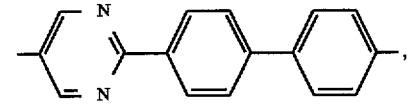

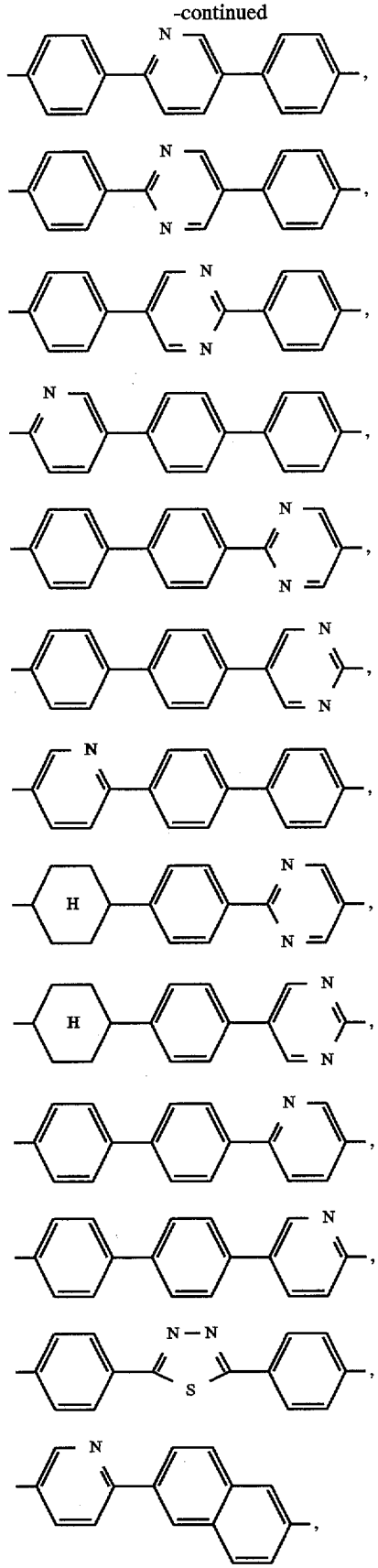
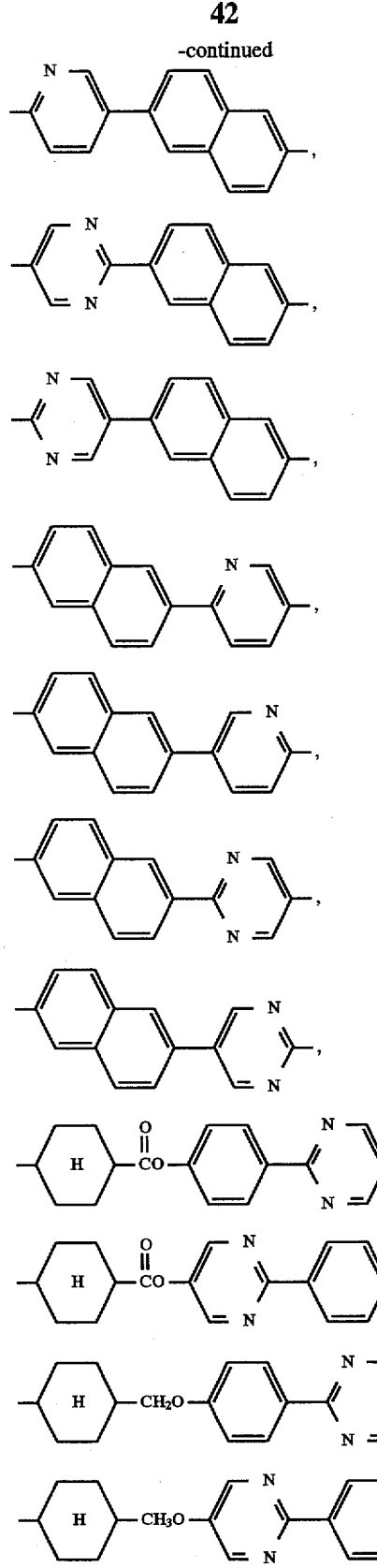
6. A liquid-crystal mixture which contains from 0.01 to 60% by weight of at least one oxiranylmethyl ether as claimed in claim 2.

7. A ferroelectric liquid-crystal mixture which contains from 0.01 to 60% by weight of at least one oxiranylmethyl ether as claimed in claim 1.

8. A ferroelectric liquid-crystal mixture which contains from 0.01 to 60% by weight of at least one oxiranylmethyl ether as claimed in claim 4.

9. A ferroelectric liquid-crystal mixture which contains from 0.01 to 60% by weight of at least one oxiranylmethyl ether as claimed in claim 5.

10. An electro-optical or fully optical component containing a liquid-crystal mixture as claimed in claim 1, 6, 7 or 8.

* * * * *